(12) United States Patent  (10) Patent No.: US 6,170,675 B1
Follman et al.  (45) Date of Patent: Jan. 9, 2001

(54) MODULAR RACK ASSEMBLY

(75) Inventors: Mark Follman, Glen Rock; Paul Thom, Montclair; David Landsberger, Caldwell, all of NJ (US)

(73) Assignee: Bel-Art Products, Inc., Pequannock, NJ (US)

(*) Notice: Under 35 U.S.C. 154(b), the term of this patent shall be extended for 0 days.

(21) Appl. No.: 09/484,808

(22) Filed: Jan. 18, 2000

(51) Int. Cl.⁷ .................................................. A47F 5/00
(52) U.S. Cl. ........................ 211/41.1; 211/41.14; 211/189
(58) Field of Search ........................... 211/40, 41.1, 41.2, 211/41.3, 41.12, 41.14, 43, 189

(56) References Cited

U.S. PATENT DOCUMENTS

| D. 160,015 | * | 9/1950 | Rauch et al. . | |
| 1,476,865 | * | 12/1923 | Weyrauch . | |
| 4,162,013 | * | 7/1979 | Tucker | 211/189 X |
| 4,600,110 | * | 7/1986 | Timor | 211/40 X |
| 4,653,649 | | 3/1987 | Holdredge, Jr. . | |
| 4,967,915 | | 11/1990 | Robson . | |
| 5,031,779 | | 7/1991 | Szenay et al. . | |
| 5,072,835 | | 12/1991 | Price, Jr. et al. . | |
| 5,370,242 | | 12/1994 | Huang . | |
| 5,370,243 | * | 12/1994 | Rosario | 211/40 |
| 5,715,948 | * | 2/1998 | Hung | 211/40 |
| 5,865,320 | | 2/1999 | Hamada . | |
| 5,931,315 | | 8/1999 | Lorentz et al. . | |

OTHER PUBLICATIONS

Bel–Air Products, Catalog 198, p. 293–346.

* cited by examiner

*Primary Examiner*—Robert W. Gibson, Jr.
(74) *Attorney, Agent, or Firm*—Lawrence G. Fridman

(57) ABSTRACT

A modular rack assembly includes a plurality of interconnected support modules sandwiched between a pair handle modules with a pair of elongate fastener assemblies securing the modules together. The length of the rack assembly may be adjusted by adding or taking away modules. Each module is of I-beam construction and is preferably integrally molded of a relatively stiff plastic material. The modules may be pigmented to provide rack assemblies of different colors for distinguishing between articles supported thereon.

20 Claims, 5 Drawing Sheets

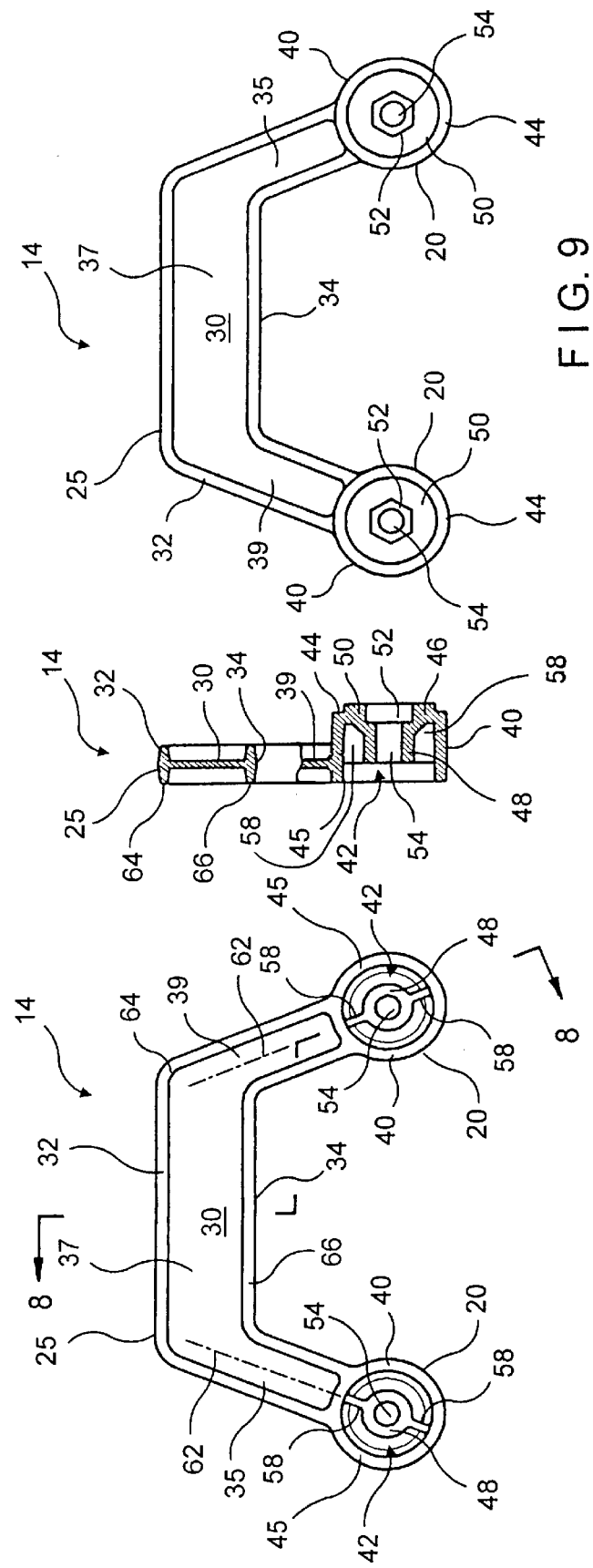

MODULAR RACK ASSEMBLY

BACKGROUND OF THE INVENTION

1. Field of the Invention

This invention relates to a rack for accommodating flat articles, and more particularly to an adjustable rack for holding gel plates of varying size and thickness used in DNA analysis.

2. Description of the Related Art

Gel plates of varying size and thickness are used in electrophoresis equipment. This equipment is designed to promote molecular separation or sequencing of various proteins found in DNA. During separation or sequencing, the proteins are introduced into a suspension located between gel-coated glass plates. When an electrical current is applied to electrodes in contact with the gel, the proteins separate from the suspension and migrate to the glass plates. This separation or sequencing is then captured on film to maintain a record. The equipment is then broken down and cleaned for reuse. During cleaning, the glass plates must be transported to a cleaning station where the gel is removed, typically with ethanol-based cleaning solutions. Each laboratory has different production requirements and thus different quantities of gel plates that need to be stored, cleaned, transported, and so on. Current racks in use are constructed of sheet plastic that are of inverted V-shaped configuration. However, these racks are not adaptable to the various needs of laboratories or other environments.

Thus, there remains a continuous need for racks that can be custom configured at each laboratory in a relatively simple, quick and efficient manner without special skills or special hand tools to thereby accommodate different plate size requirements and different holding capacities. Moreover, it would be desirable to provide racks that are easily distinguishable from each other in order to differentiate between glass plates that are dirty, pretreated, and untreated, and whether the plates are installed in the front or back of the electrophoresis equipment, and so on.

SUMMARY OF THE INVENTION

It is therefore an object of the present invention to provide a modular rack assembly that overcomes disadvantages associated with the prior art.

According to one exemplary embodiment of the invention, a rack assembly for holding a plurality of flat articles comprises a plurality of interconnecting support modules. Each support module includes a pair of spaced-apart base members and an elongate beam extending between and connected to the base members. The elongate beam is preferably I-shaped in cross section and includes a center section with a first height that is greater than a height of the base members. Each of the base members has a continuous wall that defines a hollow interior. An outer boss portion extends forwardly of a front surface of the continuous wall. The hollow interior of one support module is sized to receive the outer boss portion of an adjacent support module to thereby prevent mutual rotation of the support modules. An elongate fastener is adapted to extend through the base members to thereby secure the support modules together.

According to a further exemplary embodiment of the invention, a rack assembly for holding a plurality of flat articles comprises a plurality of interconnecting support modules. Each support module includes a pair of spaced-apart base members and an elongate beam that extends between and is connected to the base members. The elongate beam includes a center section with a first height that is greater than a height of the base members. Each of the base members has a continuous wall that defines a hollow interior, a front surface with an outer boss portion extending forwardly thereof, and an inner boss portion extending into the hollow interior from the outer boss portion. The inner boss portion includes a bore. The hollow interior of one support module is sized to receive the outer boss portion of an adjacent support module to thereby prevent mutual rotation of the support modules. An elongate fastener is adapted to extend through the bores of the inner boss portions to thereby secure the support modules together.

A pair of interconnecting handle modules may also be provided for mounting at opposite ends of interconnecting support modules. Each handle module includes a pair of spaced-apart handle base members substantially identical in construction to the base members of the support modules, and an elongate handle beam extending between and connected to the handle base members. Preferably, the elongate handle beam is I-shaped in cross section and includes a center section with a second height that is greater than the height of the base members and less than the first height. The outer boss portion of one handle module is received in the hollow interior of one of the support modules, and the outer boss portion of another of the support modules is received in the hollow interior of the other handle module.

Other objects and advantages of the invention will become apparent upon reading the following detailed description and appended claims, and upon reference to the accompanying drawings.

BRIEF DESCRIPTION OF THE DRAWINGS

The preferred embodiments of the present invention will hereinafter be described in conjunction with the appended drawings, wherein like designations denote like elements, and wherein:

FIG. 7 is a rear elevational view of a handle module that forms part of the modular rack assembly;

FIG. 8 is a cross section of the handle module taken along line 8—8 of FIG. 7;

FIG. 9 is a front elevational view of the handle module;

It is noted that the drawings of the invention are not necessarily to scale. The drawings are merely schematic representations, not intended to portray specific parameters of the invention. The drawings are intended to depict only typical embodiments of the invention, and therefore should not be considered as limiting the scope thereof. The invention will now be described with additional specificity and detail through the accompanying drawings.

DETAILED DESCRIPTION OF THE PREFERRED EMBODIMENTS

Figure 1:
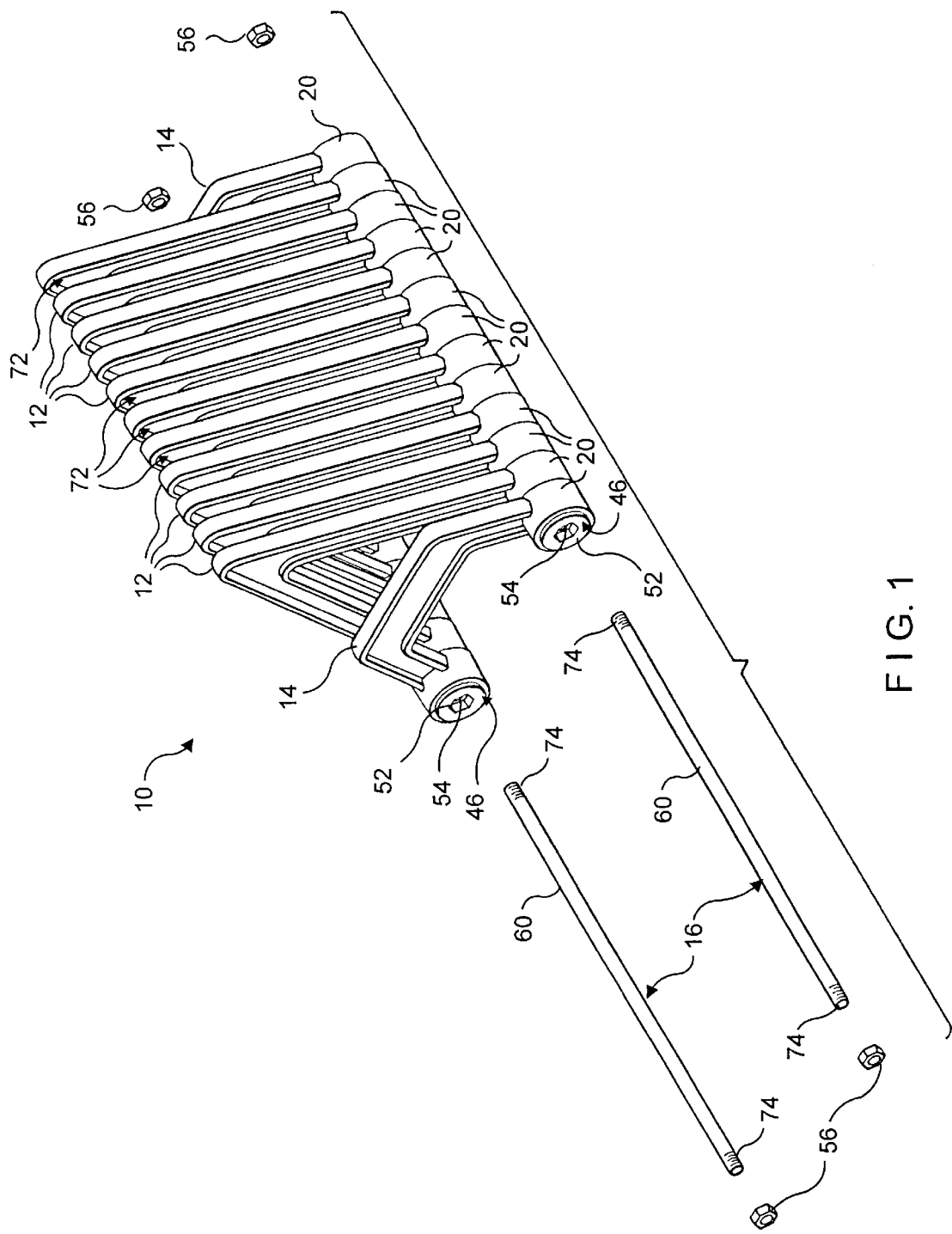
FIG. 1 is a partially exploded isometric view of a modular rack assembly according to the invention.
Figures 2, 3:
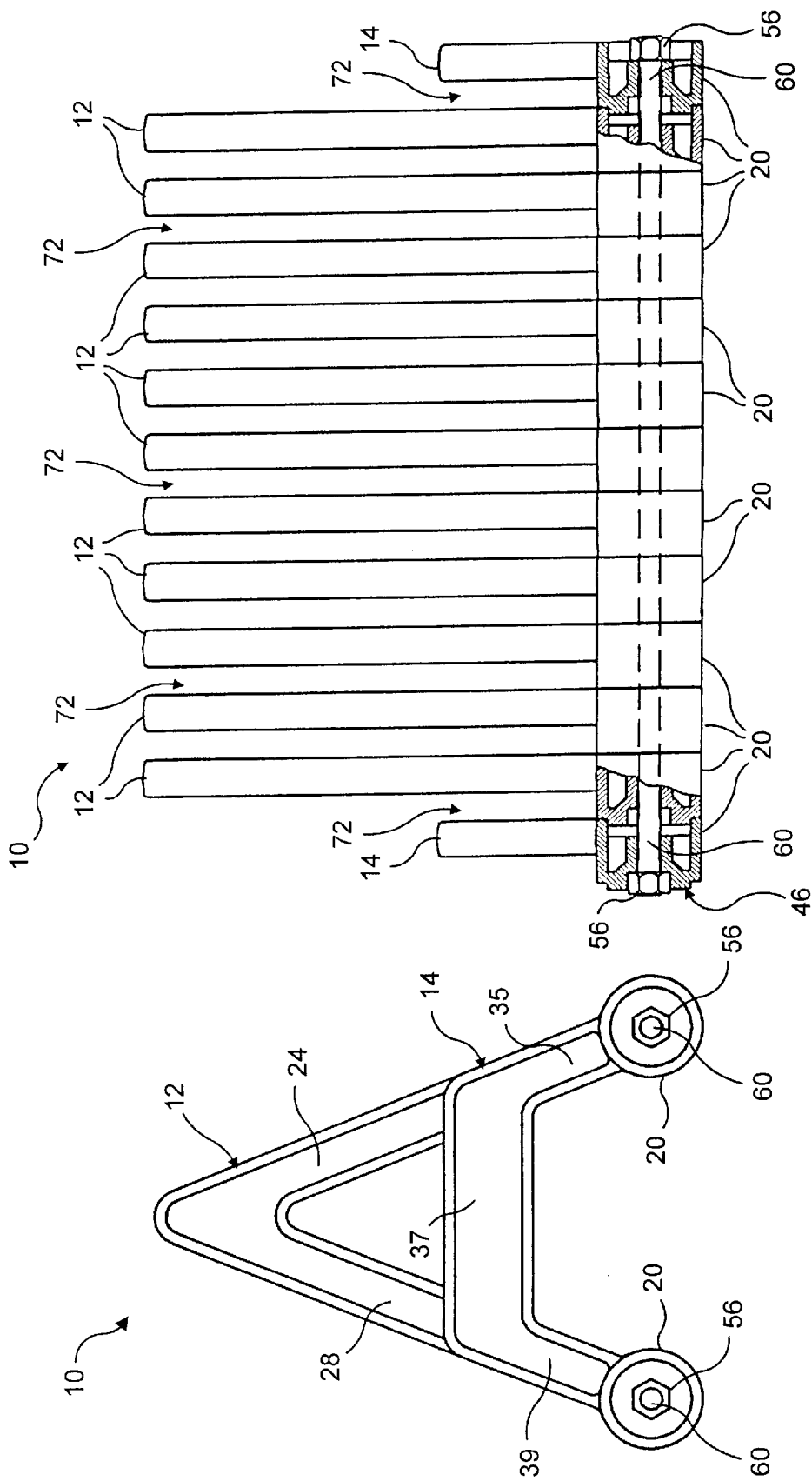
FIG. 2 is a front elevational view of the modular rack assembly.
FIG. 3 is a side elevational view of the modular rack assembly in partial cross section.

Referring now to the drawings, and to FIGS. 1 to 3 in particular, a modular rack assembly 10 includes a plurality of interconnected support modules 12 sandwiched between a pair of handle modules 14 with a pair of elongate fastener assemblies 16 securing the modules together. According to a preferred arrangement of the invention, each module 12, 14 is integrally molded of a relatively stiff, rigid plastic material, such as ABS or the like. Preferably, the material is resistant to ethanol-based cleaning solutions. The modules 12, 14 may be pigmented to provide rack assemblies 10 of different colors. This is especially advantageous for distinguishing between racks that serve different functions. For example, it may be desirous to distinguish between racks supporting glass plates used in electrophoresis equipment. The racks may thus identify plates that are clean, dirty, pretreated, and untreated, as well as front and rear glass plates, and so on.

With additional reference to FIGS. 4 to 9, each support module 12 and each handle module 14 includes a pair of spaced-apart base members 20 and an elongate beam 22 or 25 extending between and connected to the base members. The elongate beam 22 of each support module 12 is preferably of a generally inverted V-shaped configuration (FIGS. 4 to 6), while the elongate beam 25 of each handle module 14 is preferably of a generally inverted U-shaped configuration (FIGS. 7 to 9). The inverted V-shaped configuration of the support modules 12 is particularly advantageous since it maximizes air flow between glass plates or other articles inserted between the support modules to thereby promote drying of the plates. The open bottom of the inverted V also permits drainage of wash water and other liquids. As shown most clearly in FIGS. 1 to 3, the height of the support modules 12 is preferably greater than the height of the handle modules 14.

Figures 4, 5, 6:
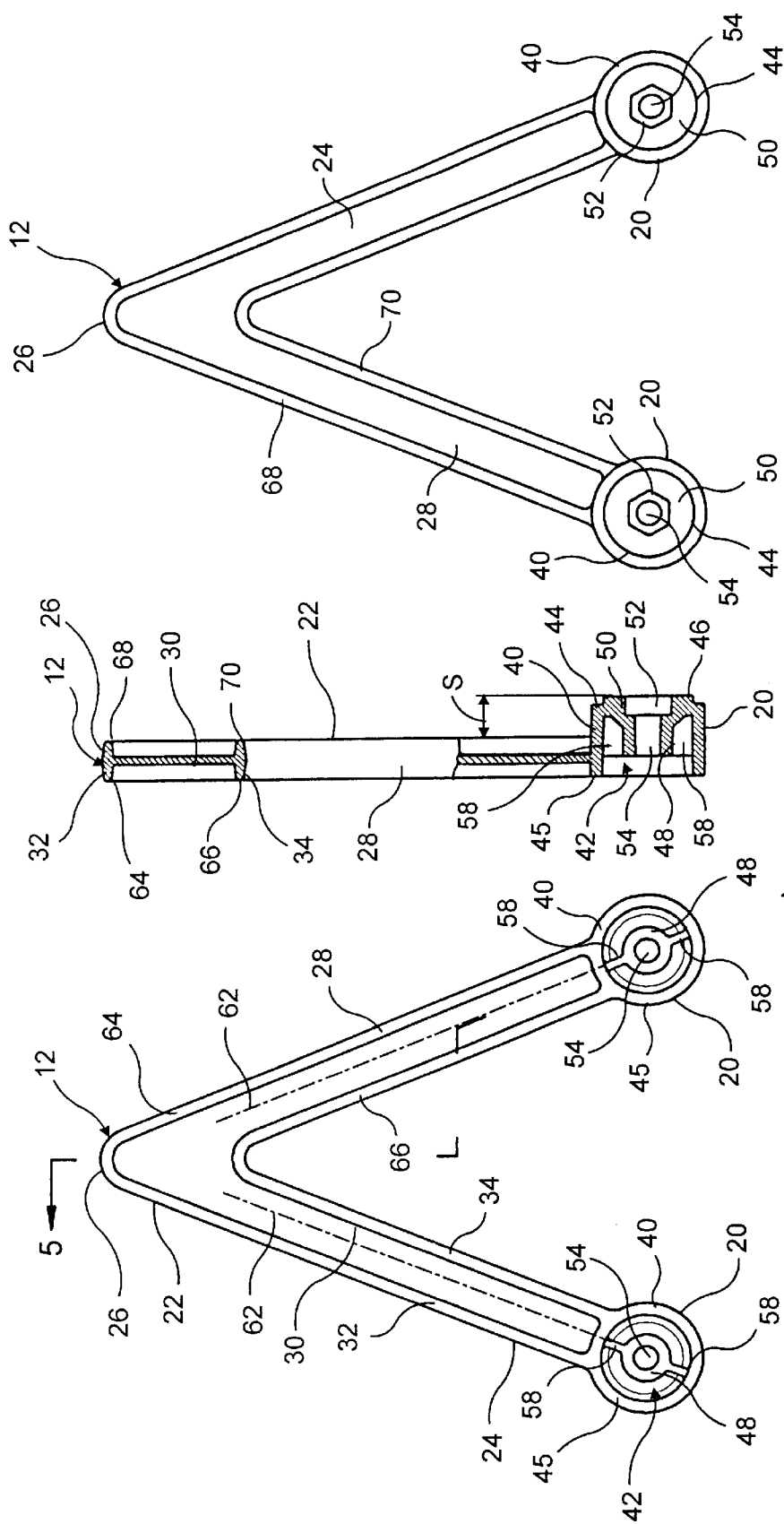
FIG. 4 is a rear elevational view of a support module that forms part of the modular rack assembly.
FIG. 5 is a cross section of the support module taken along line 5—5 of FIG. 4.
FIG. 6 is a front elevational view of the support module.

Referring to FIGS. 4 to 6, each beam 22 of the modules 12 includes a first leg 24 that extends between one of the base members 20 and an apex or center section 26, and a second leg 28 that extends between the other base member 20 and the apex 26. Preferably, the beam 22 is I-shaped in cross section and includes a center web 30 with outer and inner cross members 32, 34, respectively, extending generally transverse to the center web 30. The I-shaped arrangement of the beam 22 provides a high strength to weight ratio that minimizes bending and flexing during use. Although the generally inverted V-shaped configuration is preferred, it is to be understood that one or more of the beams 22 can be of any desired shape or configuration, such as inverted U-shaped, curved, and so on.

With reference to FIGS. 7 to 9, each beam 25 of the handle modules 14 includes a first leg 35 that extends between one of the base members 20 and a second or center leg 37, and a third leg 39 that extends between the other base member 20 and the second leg 37. The first leg 35 and third leg 39 are preferably parallel to the first leg 24 and second leg 28 of the support modules 12, respectively, as shown in FIG. 2 to thereby generate a streamlined appearance. As with the support modules 12, the beam 25 of the handle modules 14 is I-shaped in cross section and includes a center web 30 with outer and inner cross members 32, 34, respectively, extending generally transverse to the center web 30. The center leg 37 is preferably of a length and size to be easily and firmly gripped by a user for carrying the rack assembly 10 and its contents safely and securely. Although the generally inverted U-shaped configuration is preferred, it is to be understood that one or more of the beams 25 can be of any desired shape or configuration, such as inverted V-shaped, curved, and so on.

Referring again to FIGS. 4 to 9, each base member 20 of the support modules 12 and handle modules 14 includes a generally cylindrical continuous wall 40 and a front surface 44 and rear surface 45. Although the cylindrical shape of the continuous wall 40 is preferred, it is to be understood that the continuous wall may be formed into cross sectional shapes, such as square, triangular, hexagonal, and so on. In any event, the continuous wall 40 defines a hollow interior 42. An annular boss 46 is integrally formed with the front surface 44 and includes an inner boss portion 48 that extends rearwardly into the hollow interior 42 and an outer boss portion 50 that extends forwardly of the front wall 44. Preferably, the outer boss portion of each base member 20 is of the same shape as the hollow interior 42 and is sized to be snugly received in the hollow interior of a forward adjacent base member (see FIGS. 3, 10 and 11). A hexagonal-shaped depression 52 is formed in the outer boss portion 50 for receiving a threaded nut 56 (FIG. 1) or head of a fastener assembly 16. A central bore 54 extends through the annular boss 46 and is in communication with the depression 52 for receiving the shaft 60 (FIG. 1) of a fastener assembly 16. A pair of opposed support ribs 58 extend between the inner boss portion 48 and the continuous wall 40 to give strength and rigidity against bending forces that may occur when the upper end of adjacent beams in a secured rack assembly are forced toward or away from each other. Accordingly, the ribs 58 are preferably oriented along a longitudinal centerline 62 of each leg 24, 28 of the support modules 12 and each leg 35, 39 of the handle modules 14.

As shown, a rear surface 64 and 66 of the inner and outer cross members, respectively, are coplanar with the rear surface 45 of the base member 20. The front surface 44 of the base member 20 extends forwardly of front surfaces 68 and 70 of the inner and outer cross members, respectively, by a distance "S" (FIG. 5) to thereby define the spacing or slot 72 (FIG. 3) between the beams 22 or 25 of adjacent modules into which plates (not shown) or other articles will be inserted for storage, cleaning, transportation, and the like.

Figure 10:
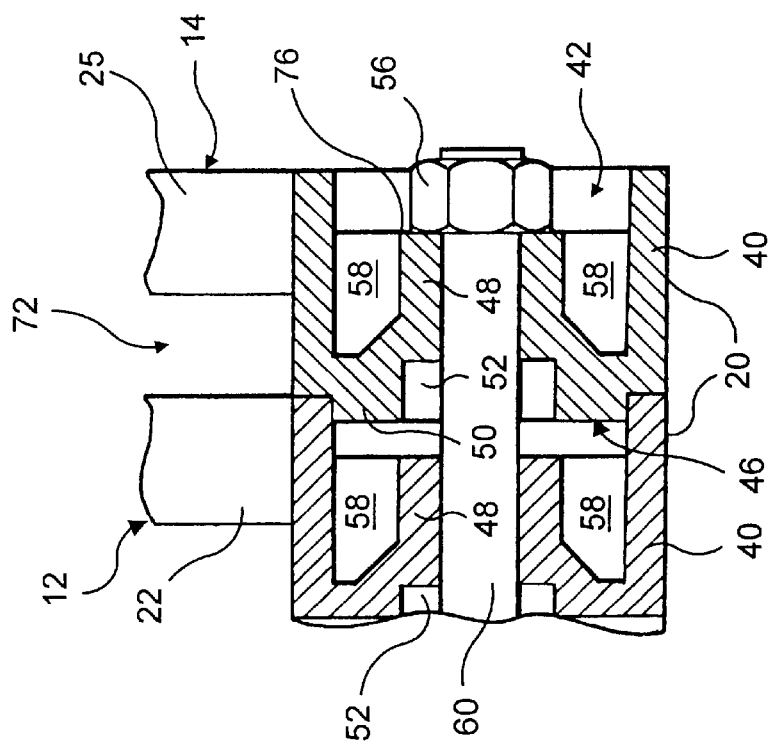
FIG. 10 is an enlarged sectional view of a forward interconnection portion of the modular rack assembly.
Figure 11:
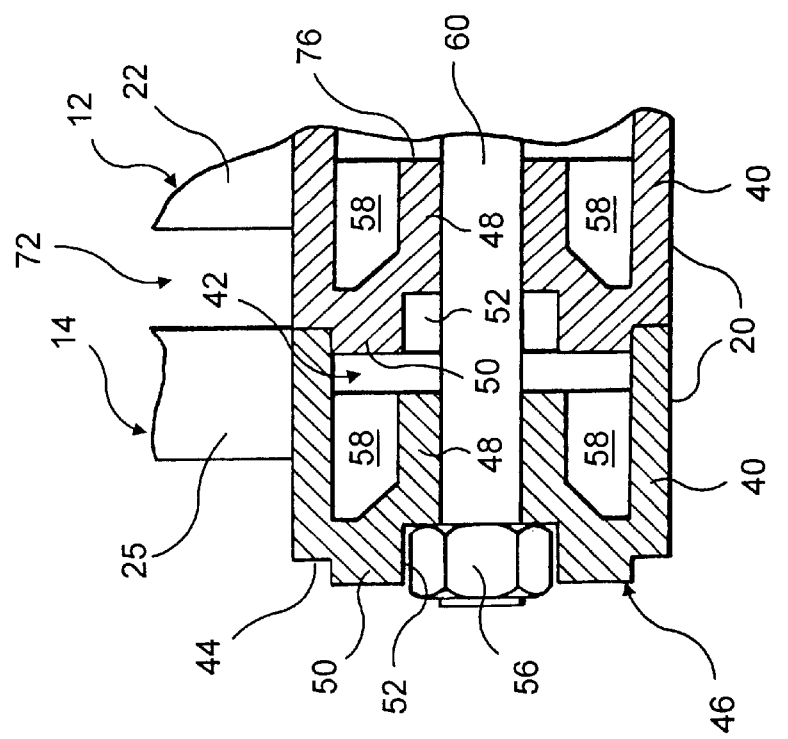
FIG. 11 is an enlarged sectional view of a rearward interconnection portion of the modular rack assembly.

With particular reference to FIGS. 1, 10 and 11, the modular rack assembly 10 is assembled by aligning the base members of one support module 12 with the base members of another support module 12 and/or handle module 14, until the outer boss portions 50 of one module 12, 14 are received in the hollow interior 42 of an adjacent module 12, 14. In this manner, the bores 54 of adjacent base members 20 are aligned. A stud 60 with threaded ends 74 is then inserted through the bores 54 and a nut 56 is secured on each end 74. When tightened, the forward nuts 56 are seated in the depression 52 and the rear nuts 56 are pressed against a rear surface 76 of the inner boss portion 48 with the rear nuts 56 received in corresponding hollow interiors 42, while the front surface 44 of a rear base member 20 is in contact with the rear surface 45 of an adjacent forward base member 20. The depressions 52 are preferably similar in shape to the forward nuts 56 to thereby prevent rotation of the forward nuts during tightening of the rear nuts. With the outer boss portions of one module 12, 14 received in the hollow interior 42 of an adjacent module 12, 14, the modules are secured together against separation and mutual rotation. If desired, washers and/or lock washers (not shown) may be provided between the nuts 56 and the base members 20. Instead of a stud 60 and opposed nuts 56, a bolt and nut combination or other fastening means may be provided.

The above-described arrangement is especially suitable for laboratories or other environments where different numbers of slots 72 are needed. Any number of support modules 12 can be assembled together, with or without the handle modules 14. The studs 60 can vary in size accordingly. When assembled without handle modules 14, the rack assembly 10 may serve as a dedicated drying and/or storage rack.

Although the base members 20 for both the support modules 12 and handle modules 14 are shown as similar in length, it is to be understood that varying lengths may be provided for one or more modules to thereby vary the spacing of the slots 72 between adjacent modules. This is especially advantageous when plates or other articles of different thickness are to be inserted in the slots. Moreover, the height of the apex 26 of the support modules and/or the height of the second leg 37 of the handle modules can vary, as well as the spacing between base members 20 of the same module.

From the foregoing, it can be seen that rack assemblies are provided that can be custom configured at each laboratory in a relatively simple, quick and efficient manner without special skills or special hand tools to thereby accommodate different plate size requirements and different holding capacities. It is also readily evident that racks with different pigments are easily distinguishable from each other in order to differentiate between gel plates that are dirty, pretreated, and untreated, and whether the plates are installed in the front or back of the electrophoresis equipment, and so on.

It is to be understood that the terms inner, outer, front, rear, upper, lower, and their respective derivatives as used throughout the specification and/or claims denote relative, rather than absolute orientations and/or positions.

While the invention has been taught with specific reference to the above-described embodiments, those skilled in the art will recognize that changes can be made in form and detail without departing from the spirit and the scope of the invention. Thus, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The embodiments for which an exclusive property or privilege is claimed are defined as follows:

1. A rack assembly for holding a plurality of flat articles, the rack assembly comprising:
    a plurality of interconnecting support modules, each support module including a pair of spaced-apart base members and an elongate beam extending between and connected to the base members, the elongate beam being I-shaped in cross section and including a center section with a first height that is greater than a height of said base members, each of said base members having a continuous wall defining a hollow interior, a front surface with an outer boss portion extending forwardly thereof and a rear surface, the hollow interior of one support module being sized to receive the outer boss portion of an adjacent support module to thereby prevent mutual movement of said support modules; and
    an elongate fastener adapted to extend through said base members to thereby secure said support modules together.

2. A rack assembly according to claim 1, and further comprising a pair of interconnecting handle modules adapted for mounting at opposite ends of said plurality of interconnecting modules, each of said handle modules including a pair of spaced-apart handle base members substantially identical in construction to said base members of said support modules, and an elongate handle beam extending between and connected to the handle base members, the elongate handle beam being I-shaped in cross section and including a center section with a second height that is greater than the height of said base members and less than the first height, the outer boss portion of one handle module being received in the hollow interior of one of said support modules, and the outer boss portion of another of said support modules being received in the hollow interior of the other handle module.

3. A rack assembly according to claim 2, wherein the elongate beam of each support module is of a generally inverted V-shaped configuration.

4. A rack assembly according to claim 3, wherein the elongate beam of each handle module is of a generally inverted U-shaped configuration.

5. A rack assembly according to claim 2, wherein the elongate beam of each handle module is of a generally inverted U-shaped configuration.

6. A rack assembly according to claim 1, wherein the elongate beam of each support module is of a generally inverted V-shaped configuration.

7. A rack assembly according to claim 1, wherein each base member further comprises an inner boss portion extending into said hollow interior from the outer boss portion, the inner boss portion including a bore through which said elongate fastener extends.

8. A rack assembly according to claim 7, wherein the front surfaces of the base members associated with said one support module abuts the rear surfaces of the base members associated with said adjacent support module.

9. A rack assembly according to claim 7, wherein each base member includes at least one rib extending from the inner boss portion for supporting the inner boss portion against bending forces transmitted through the elongate beam.

10. A rack assembly according to claim 9, wherein the at least one rib is oriented along a longitudinal centerline of the elongate beam.

11. A rack assembly according to claim 10, wherein the elongate beam of each support module is of a generally inverted V-shaped configuration.

12. A rack assembly according to claim 1, wherein the front surfaces of the base members associated with said one support module abuts the rear surfaces of the base members associated with said adjacent support module.

13. A rack assembly for holding a plurality of flat articles, the rack assembly comprising:
    a plurality of interconnecting support modules, each support module including a pair of spaced-apart base members and an elongate beam extending between and connected to the base members, the elongate beam including a center section with a first height that is greater than a height of said base members, each of said base members having a continuous wall defining a hollow interior, a front surface with an outer boss portion extending forwardly thereof and a rear surface, an inner boss portion extending into said hollow interior from the outer boss portion, the inner boss portion including a bore, the hollow interior of one support module being sized to receive the outer boss portion of an adjacent support module to thereby prevent mutual movement of said support modules; and
    an elongate fastener adapted to extend through the bores of said inner boss portions to thereby secure said support modules together.

14. A rack assembly according to claim 13, and further comprising a pair of interconnecting handle modules adapted for mounting at opposite ends of said plurality of interconnecting support modules, each of said handle modules including a pair of spaced-apart handle base members substantially identical in construction to said base members of said support modules, and an elongate handle beam extending between and connected to the handle base members, the elongate handle beam including a center section with a second height that is greater than the height of said base members and less than the first height, the outer boss portion of one handle module being received in the hollow interior of one of said support modules, and the outer boss portion of another of said support modules being received in the hollow interior of the other handle module.

15. A rack assembly according to claim 14, wherein the beam of each support module and the beam of each handle module are substantially I-shaped in cross section.

16. A rack assembly according to claim 13, wherein each base member includes at least one rib extending from the inner boss portion for supporting the inner boss portion against bending forces transmitted through the elongate beam.

17. A rack assembly according to claim 16, wherein the at least one rib is oriented along a longitudinal centerline of the elongate beam.

18. A rack assembly according to claim 17, wherein the elongate beam of each support module is of a generally inverted V-shaped configuration.

19. A rack assembly according to claim 13, wherein the front surfaces of the base members associated with said one support module abuts the rear surfaces of the base members associated with said adjacent support module.

20. A rack assembly for holding a plurality of flat articles, the rack assembly comprising:

a plurality of interconnecting support modules, each support module including a pair of spaced-apart base members and an elongate beam extending between and connected to the base members, the elongate beam being I-shaped in cross section and of a generally inverted V-shaped configuration with an apex located at a first height, each of said base members having a continuous wall defining a hollow interior, a front surface with an outer boss portion extending forwardly thereof and a rear surface, an inner boss portion extending into said hollow interior from the outer boss portion, the inner boss portion including a bore;

at least one rib extending between the inner boss portion and the continuous wall for supporting the inner boss portion against bending forces transmitted through the elongate beam, the at least one rib being oriented along a longitudinal centerline of the elongate beam;

a pair of interconnecting handle modules mounted at opposite ends of said plurality of interconnecting support modules, each of said handle modules including a pair of spaced-apart handle base members substantially identical in construction to said base members of said support modules, and an elongate handle beam extending between and connected to the handle base members, the elongate handle beam being I-shaped in cross section and of a generally inverted U-shaped configuration with an upper handle section having a second height that is less than the first height;

wherein the hollow interior of the base members of one module is sized to receive the outer boss portions of the base members of an adjacent module to thereby prevent mutual rotation of said modules, with the front surfaces of the base members associated with said one module abutting the rear surfaces of the base members associated with said adjacent module; and an elongate fastener extending through the bores of aligned inner boss portions to thereby secure said modules together.

* * * * *